United States Patent [19]

Kuhrts

[11] Patent Number: 5,023,245

[45] Date of Patent: * Jun. 11, 1991

[54] IMPROVED NIACIN FORMULATION

[75] Inventor: Eric H. Kuhrts, Santa Barbara, Calif.

[73] Assignee: Hauser-Kuhrts, Inc., Santa Barbara, Calif.

[*] Notice: The portion of the term of this patent subsequent to Oct. 23, 2007 has been disclaimed.

[21] Appl. No.: 440,728

[22] Filed: Nov. 22, 1989

Related U.S. Application Data

[63] Continuation-in-part of Ser. No. 119,188, Nov. 10, 1987, abandoned, and a continuation-in-part of Ser. No. 178,472, Apr. 7, 1988, and a continuation-in-part of Ser. No. 212,715, Jun. 28, 1988, Pat. No. 4,965,252, and a continuation-in-part of Ser. No. 212,607, Jun. 28, 1988, Pat. No. 4,911,917.

[51] Int. Cl.$^5$ ............... A61K 31/715; A61K 31/33; A61K 9/14

[52] U.S. Cl. ............... 514/54; 514/183; 514/188; 514/909; 514/911; 514/824; 424/439; 424/464; 536/114; 536/123

[58] Field of Search ............ 514/183, 54, 188, 911, 514/951, 909, 824; 424/439, 464; 536/114, 123

[56] References Cited

U.S. PATENT DOCUMENTS

| | | | |
|---|---|---|---|
| 3,843,778 | 10/1974 | Diamond et al. | 424/498 |
| 4,166,902 | 9/1979 | Ferruti | 536/48 |
| 4,237,118 | 12/1980 | Howard | 424/630 |
| 4,764,374 | 8/1988 | Grimberg | 424/601 |

FOREIGN PATENT DOCUMENTS 2021948 12/1979 United Kingdom.

OTHER PUBLICATIONS

Drug Facts and Comparisons, 1988, p. 19 plus cover sheet.

*Primary Examiner*—Ronald W. Griffin
*Attorney, Agent, or Firm*—Gordon W. Hueschen

[57] ABSTRACT

An antihyperlipidemic pharmaceutical or dietary supplement composition for oral use consisting essentially of a combination of niacin and a gel-forming dietary fiber, and a method of lowering cholesterol levels with such oral pharmaceutical composition, or by the simultaneous oral administration of the active ingredients thereof, which eliminates the usual undesirable flushing and itching side effects of niacin while effectively lowering cholesterol levels, especially LDL cholesterol levels, is disclosed.

40 Claims, No Drawings

IMPROVED NIACIN FORMULATION

The present application is a continuation-in-part of my prior-filed co-pending applications Ser. No. 119,188, filed Nov. 10, 1987, now abandoned; Ser. No. 178,472, filed Apr. 7, 1988; Ser. No. 212,715, filed June 28, 1988, now U.S. Pat. No. 4,965,252 and Ser. No. 212,607, filed June 28, 1988, now U.S. Pat. No. 4,911,917.

BACKGROUND OF THE INVENTION

1. Field of Invention

Antihyperlipidemic pharmaceutical or dietary supplement compositions and method of treating hyperlipidemic conditions therewith; combination compositions and therapy employing niacin and another active antihyperlipidemic principle, namely, gel-forming dietary fiber, which eliminate the usual undesirable side effects of niacin.

2. Background of the Invention and Prior Art

Nicotinic acid was the only agent studied by the Coronary Drug Project which produced a significant decrease in coronary events. Coronary Drug Project Research Group: Clofibrate and Niacin and Coronary Heart Disease. JAMA 231:360 (1975). This research demonstrated that niacin lowers blood cholesterol on an average by nine percent and reduces the recurrence rate of myocardial infarction by 29%. The study involved more than 8,000 individuals and was conducted over a period of six (6) years. The usual dosage range for niacin therapy is 3 to 6 grams per day, which dosage is capable of lowering cholesterol level from 10 to 25%, triglyceride level by 45 to 50%, and elevating HDL cholesterol by 15 to 20%.

In a paper in the Journal of Lipid Research 22:24–36 (1981) entitled "Influence of Nicotinic Acid on Metabolis of Cholesterol and Triglycerides in Man", it is stated as follows:

"Although the magnitude of plasma lipid lowering by nicotinic acid can be appreciable, its usefulness has been limited by certain disagreeable side effects such as flushing of the face and other skin reactions."

Although the actual mechanisms by which niacin reduces cholesterol and triglycerides is not completely known, it is known that niacin does produce these effects and that niacin, moreover, has an ability to increase the amount of the protective form of cholesterol, namely, HDL cholesterol.

A major shortcoming of niacin is the necessity of administering large doses of niacin to effectively lower cholesterol level. Most subjects treated will experience accompanying side effects of flushing, prickling of the skin, and itching when they begin niacin, when the dosage is increased, or when the treatment is temporarily terminated and then commenced once more at the same dose. Ordinarily, it is necessary for a subject to gradually increase the dosage of niacin to a three to six gram per day dosage level over a period of months, starting with one 50 mg tablet three times daily for a total dose of 150 mg per day, to avoid being overwhelmed with the unpleasant side effects.

The prior art is replete with reports of the reduction of cholesterol levels and control of cholesterol levels in a subject in need of the same employing niacin (nicotinic acid) and of the undesirable side effects ordinarily produced when an effective amount of niacin is employed for such purpose. The side effects include flushing and itching, and it is well documented in the literature that such flushing, itching, and so on is not eliminated by intermittent niacin therapy, and generally reappears even when the therapy is interrupted and reinstituted. Although the degree or intensity of such side effects varies from patient to patient, it is frequently observed that such therapy cannot be applied in the case of various patients who are hypersensitive to the niacin or to the side effects which result in such patients upon oral administration thereof.

The present status of niacin treatment has been capsulated by Luria in Arch Intern Med 148, pp. 2493–2495 (Nov 1988) in the following words:

"Its use has been clinically stymied, however, by side effects.", so that only low dosages may be administered with safety and patient acceptability, although even this latter is not a certainty even with low dosages over an extended perod.

Numerous other approaches to the lowering of cholesterol in a subject in need thereof have been proposed. For example, cholestyramine and other drugs which theoretically affect the bile acid pool and pull cholesterol out of the bloodstream according to the postulated mechanism are also available as are the gel-forming dietary fiber materials, such as guar gum and the like. Guar gum has been suggested as a dietary supplement fiber having an effect on cholesterol upon ingestion, but having a somewhat reduced effect when compared to bile acid-binding agents such as cholestyramine. Although the effect of guar gum is clear, its mechanism of action as a plasma cholesterol-lowering agent is unclear. What is clear, however, is that guar gum has no specific affinity for either cholesterol or for bile salts and that it does not act as a bile acid-binding agent in the manner of cholestyramine or the like, being 60–70 percent less effective in this regard, but yet being able to lower cholesterol levels almost as well as cholestyramine.

Dietary supplements or regimens combining oat bran (e.g., 100 grams per patient per day) and niacin have been recommended, but there has been no evidence or suggestion that such combination dietary treatment or approach has any effect upon the undesirable side effects of niacin, least of all at cholesterol-lowering dosages or intakes. Although it has been reported that side effects and especially gastric irritation may be somewhat reduced by taking the medication with meals and by the use of antacids or by combined therapy with colestipol, a bile acid-sequestering resin having proton-binding properties, its side effects continue to hamper its general applicability in cholesterol lowering and poor patient compliance often results because of these side effects.

It is accordingly reported that "Continuous flushing, resulting from harmless dilation of skin capillaries, occurs in most individuals at onset of treatment and when dosage is increased.—Patients should be warned that if several doses are missed, the flushing will recur.—Gastric irritation is also frequently encountered.—"

Since niacin, at a dosage level of three to six grams per day, is very effective in reduction of undesirable cholesterol levels, which reportedly fall by a mean of approximately 22% during some controlled clinical evaluations, it would be highly desirable to provide a way in which this valuable cholesterol-lowering material could be more generally applied without fear of or limitation by the said undesirable side effects, and the present invention addresses this problem, which has heretofore had no satisfactory solution, by combined therapy employing also guar gum, or another gel-forming natural dietary fiber which itself is a dietary supplement and which itself may be known to produce a cholesterol-lowering effect, but which unpredictably, as found according to the present invention, essentially eliminates or at least very substantially reduces the usual niacin side effects when administered simultaneously and preferably in a combination composition therewith.

Combination therapy employing colestipol, a bile acid sequestrant, together with niacin or its prodrug clofibrate, produced reduction in cholesterol levels as expected, which were greater when niacin was used together with colestipol rather than its prodrug clofibrate, but care still had to be taken to "mitigate the prostaglandin-mediated cutaneous flushing often associated with niacin", aspirin therefore being administered a half hour before each dose of niacin for this purpose. Combination therapy involving Lovastatin, plus a resin such as cholestyramine or colestipol, and niacin has also been suggested, it being reported that the Lovastatin reduced the amount of resin and niacin required to produce satisfactory results, and providing a possible powerful therapy for severe familial hypercholesterolemia, although such bile acid-sequestering resins are suspect as possibly binding and at least partially inactivating niacin as well. In any case, the combination of niacin plus the already-established guar gum or other gel-forming dietary fiber supplement (fiber intake already having been established as "inversely related to all-cause mortality"), as provided by the present invention, would appear to be a much simpler solution to the problem of the undesirable niacin side effects, while at the same time providing effective double-barrel cholesterol-lowering effect and results, than any combination, method-of-treating, or dietary supplement approach which has been suggested previously.

Guar gum is derived from a leguminous plant which bears bean-like pods containing six to nine seeds, known as *Cyanopsis tetragonoloba*. The seed is 40–46% germ, 38–45% endosperm, and 14–16% husk. Guar gum is prepared by first removing the husk and sperm components and then is derived essentially from the endosperm. It is marketed commercially in different grades and is chemically a galactomannan with galactose on every other mannose unit, having a molecular weight of approximately 220,000. It disperses in cold water to form a viscous pseudoplastic sol, the viscosity of which can be enhanced with heating, and it has an extremely high viscosity, which is fivefold higher per unit weight than starch, and is commercially available in various grades of dispersibility, viscosity, and thickening power, being generally packaged in powder form which requires dispersion in water. The problem of dispersing the guar gum in water is one which confronts one desiring to prepare a drinkable dispersion thereof, and also one who desires to disperse the guar gum internally upon oral ingestion, especially when most rapid action is desired. Although the mechanism of action as a plasma cholesterol-lowering agent of guar gum is unclear, it is clear that both niacin (nicotinic acid) and guar gum have been known to be effective cholesterol-lowering entities for at least twenty (20) years but, up to the time of this invention, no one has disclosed or even suggested that a combination of guar gum or any other gel-forming dietary fiber with niacin would virtually eliminate the unpleasant and normally limiting side effects of niacin in addition to providing enhanced cholesterol-lowering effect.

A Dialog search from the U.S. Patents data base for niacin for U.S. Patent Abstracts 1971–81, 1982–1987, and weekly from 12/87 through the middle of February 1988, turned up a few niacin prodrugs with or without allegedly reduced side effects and U.S. Pat. No. 4,166,902 relating to high polymers containing nicotinic acid in which nicotinic acid radicals are bound through covalent ester bonds which gradually hydrolyze in a biological environment by setting free nicotinic acid, and which allegedly have a therapeutic activity similar to that of nicotinic acid itself but longer lasting and with the elimination or least reduction of "collateral effects", the product of this patent apparently being some sort of a "depo" nicotinic acid-containing material, but of course the question remains whether the slow release of nicotinic acid as disclosed in this patent will provide adequate niacin levels for effective cholesterol lowering in practice. At any rate, this patent merely emphasizes the continued existence of the problem of niacin side effects and allegedly provides one approach to its possible solution, being in no way suggestive of the entirely different solution to the problem discovered by the present applicant.

For purposes of definition in this specification, the term "dietary fiber" is defined as "remnants of plant cells resistant to hydrolysis by the alimentary enzymes of man, the group of substances that remain in the ileum but are partly hydrolyzed by bacteria in the colon", according to JAMA 262, pp. 542–546 No. 4 (July 28, 1989) Council Report entitled "Dietary Fiber and Health", at page 542. This article, moreover, gives considerable information as to what constitutes a "dietary fiber" and is accordingly incorporated herein by reference.

Gel-forming dietary fibers include mucillages, plant gums, pectins or pectic substances, and lignin, all of which are endogenous compounds of plant materials which are resistant to digestion by enzymes in the monogastric stomach or small intestine. Chemically, nearly all of these plant materials are carbohydrates composed of repeating monosaccharide (sugar) units. Disaccharides have two sugar units, oligosaccharides three to twelve, and polysaccharides may contain a million or more. The water-soluble fractions of these substances form gels in the stomach and intestinal tract and lower serum cholesterol.

Gums and mucillages have no common structure but are polysaccharides containing several sugars with alternating monomer structures, and may or may not contain uronic acids. There are many gums found in plants and cereal grains. Guar and locust bean gums are galactomannans, whereas gum arabic is an acidic polymer of galactose and rhammose. Oat and barley contain gums, but are not practical for use in the present application because of the low percentage of active gums per weight volume. Large amounts of oat bran (e.g., 100 grams per day) are also required to lower serum cholesterol. Most of the gums in the present application are effective at much lower dosages. Suitable gums include, inter alia, besides guar gum, the following: locust bean gum, acacia gum, gum arabic, xanthan gum, carrageenan gum, karaya gum, tragacanth gum, and ghatti gum.

Pectin substances or pectins are mixtures of polysaccharides of partially methylated and 1,4-D galacturonic acid units with side chains containing arabinose, galactose, xylose, and rhammose. They are contained in many fruits and vegetables as well as other plants.

Other suitable gel-forming dietary fibers include psyllium husks, algal polysaccharides, glucomannan, and agar, to name a few. Lignin is a non-carbohydrate polymer of aromatic plant alcohols comprising oxygenated phenylpropane units. As a plant matures, more lignin is produced, which acts as a sort of cement as it hardens and holds together other plant cell wall constituents. Lignin passes through the digestive tract with very little change.

As already mentioned, a recent review of dietary fiber which mentions these substances is contained in the following reference: Dietary Fiber and Health, JAMA 262: 542-546 (1989), from the Council on Scientific Affairs, American Medical Association.

OBJECTS OF THE INVENTION

It is an object of the present invention to provide a method of lowering cholesterol, especially LDL cholesterol, in a subject in need of the same, by the employment of nicotinic acid (niacin) in combination with guar gum or another gel-forming dietary fiber, which is highly effective for its intended purpose and which has the further advantageous and unpredictable effect of eliminating or substantially reducing the usual flushing and related side effects of niacin. A further object of the invention is the provision of such a method wherein the niacin and the guar gum or another gel-forming dietary fiber are administered simultaneously. An additional object of the invention is the provision of a combination composition comprising both niacin and guar gum or another gel-forming dietary fiber which is useful for the aforesaid purpose. A still further object of the invention is the provision of such a method wherein a soluble mineral salt, especially a physiologically-acceptable soluble magnesium salt, is also administered simultaneously with the active ingredients niacin and guar gum or another gel-forming dietary fiber, and a combination composition of the active ingredients niacin and guar gum or another gel-forming dietary fiber comprising also a soluble, e.g., magnesium, salt. Still a further object of the present invention is the provision of such a method and such a combination composition which may be employed in the reduction of cholesterol levels either as or as a part of a medical or a pharmaceutical regimen or therapy for the reduction of cholesterol levels in a subject in need of the same, or as a food supplement for the effective reduction of cholesterol levels in a subject in need of the same according to the current practice of providing guar gum or other gel-forming fibrous material, i.e., dietary fiber, according to good-health dietary practices for or by a subject desiring to reduce cholesterol levels to, or maintain the same at, levels which are considered to be acceptable and/or relatively safe from a dietary or medical standpoint. Further objects of the invention will become apparent hereinafter, and still others will be obvious to one skilled in the art to which this invention pertains.

SUMMARY OF THE INVENTION

In summary then, the present invention comprises, inter alia, the following, singly or in combination:

An oral antihyperlipidemic composition of nicotinic acid characterized by reduced flushing effect comprising as active ingredients nicotinic acid and guar gum or another gel-forming dietary fiber; such a composition wherein the composition contains at least about 50 mg of nicotinic acid; such a composition wherein the amount of nicotinic acid is at least about 50 mg and the amount of guar gum or another gel-forming dietary fiber is at least about 250 mg; such a composition wherein the amount of nicotinic acid is at least about 50 mg and the amount of guar gum or another gel-forming dietary fiber is at least about 400 mg, in capsule or tablet form; such a composition wherein the amount of nicotinic acid is at least about 50 mg and the amount of guar gum or another gel-forming dietary fiber is at least about 400 mg, comprising also an antacid; such a composition comprising a physiologically-acceptable magnesium salt; such a composition comprising an orally-ingestible non-toxic mineral salt capable of dissolution in the gastric fluid; such a composition wherein the mineral salt is selected from the group consisting of calcium carbonate, magnesium carbonate, and potassium carbonate; such a composition wherein the active ingredients are in powder or granular form and comprising also a quantity of a food-grade acid (also in powder or granular form) which is effective in extending the time for gelation of the resulting mix upon addition of water; such a composition wherein the food-grade acid is selected from the group consisting of citric acid, ascorbic acid, tartaric acid, and malic acid; and such a composition comprising about 400-500 mg guar gum or another gel-forming dietary fiber, about 80-150 mg niacin, and about 80-100 mg magnesium carbonate.

Moreover, a method of combating hyperlipidemia in a subject in need of the same using nicotinic acid characterized by reduced flushing effect comprising the step of simultaneously administering orally to the said subject both nicotinic acid and guar gum or another gel-forming dietary fiber; such a method comprising the step of administering orally to the said subject both nicotinic acid and guar gum or another gel-forming dietary fiber in the form of a pharmaceutical composition containing both active ingredients; such a method comprising the step of administering orally to the said subject both nicotinic acid and guar gum or another gel-forming dietary fiber in the form of a pharmaceutical composition containing both active ingredients in capsule or tablet form; such a method comprising the step of administering orally to the said subject both nicotinic acid and guar gum or another gel-forming dietary fiber in the form of a pharmaceutical composition containing both active ingredients in capsule or tablet form comprising also an antacid; such a method wherein a single dosage comprises about 300-1000 mg of niacin and about 1.5-6 g of guar gum or another gel-forming dietary fiber; such a method wherein a single dosage comprises about 300-1000 mg niacin, about 1.5-6 g of guar gum or another gel-forming dietary fiber, and about 300-500 mg of a physiologically-acceptable magnesium salt; such a method wherein a dosage unit comprises at least about 250 mg guar gum or another gel-forming dietary fiber and at least about 50 mg niacin; such a method wherein a single dose comprises at least about 2 g guar gum or another gel-forming dietary fiber and at least about 350 mg of niacin; such a method wherein a daily dose comprises at least about 6 g guar gum, at least about 1 g niacin, and at least about 1 g magnesium carbonate; such a method wherein an orally-ingestible non-toxic mineral salt capable of dissolution i the gastric fluid is simultaneously orally administered; such a method wherein a physiologically-acceptable magnesium salt is also simultaneously orally administered; such a method wherein the physiologically-acceptable magnesium salt is magnesium carbonate; such a method wherein the active ingredients are in powder or granular form and wherein a quantity of a food-grade acid (also in powder or granular form) which is effective in extending the of the resulting mix upon addition of water is also simultaneously orally administered, and such a method wherein the mineral salt is selected from the group consisting of calcium carbonate, magnesium carbonate, and potassium carbonate.

Fundamentally, an oral antihyperlipidemic composition of nicotinic acid, having a reduced flushing effect, consisting essentially of an effective antihyperlipidemic amount of nicotinic acid and an effective cutaneous-flushing-reducing amount of a gel-forming dietary fiber, and a method for reducing the cutaneous flushing caused by the administration of an effective antihyperlipidemic amount of nicotinic acid to a patient suffering from hyperlipidemia, consisting essentially of the step of simultaneously orally administering to said patient an effective cutaneous-flushing-reducing amount of a physiologically-acceptable gel-forming dietary fiber and an effective antihyperlipidemic amount of nicotinic acid.

Moreover, such a composition wherein the mineral salt is a pharmacologically-acceptable mineral salt capable of dissolution in the gastric fluid with release of a gas; such a composition wherein the gas is carbon dioxide; such a method wherein the mineral salt is a pharmacologically-acceptable mineral salt capable of dissolution in the gastric fluid with release of a gas; such a method wherein the gas is carbon dioxide; such a composition wherein the mineral salt is a carbonate or bicarbonate; such a method wherein the mineral salt is a carbonate or bicarbonate, and such a method wherein a daily dose comprises at least about 6 g dietary fiber and at least about 1 g niacin.

GENERAL DESCRIPTION OF THE INVENTION

The invention, in general, is set forth under "Objects of the Invention" and "Summary of the Invention" but, in short, comprises the combination with niacin of guar gum or another gel-forming dietary fiber, some of which are known to be effective antihypercholesterolemic agents, with the resulting effect that an extremely effective oral antihypercholesterolemic combination is provided, preferably in a single-dosage unit form. Alternatively, the two active ingredients may be orally administered simultaneously although administration of both together in a combination composition is preferred. In addition to the desired and augmented antihypercholesterolemic effect of the combination and combination therapy of the present invention, the usual cutaneous flushing, resulting in itching or prickling of the skin, as well as bright-red blushing, which ordinarily results from harmless dilation of the skin capillaries in the course of niacin therapy and which frequently manifests itself even at a niacin dose as low as 50 mg, has unpredictably been found to be greatly reduced or essentially eliminated when the niacin is administered or ingested in combination with the guar gum or other gel-forming dietary fiber, the ratio of the guar gum or other gel-forming dietary fibers to the nicotinic acid preferably being approximately five parts of fiber to one part of nicotinic acid on a weight basis, although broader ranges are of course effective. Advantageously, a metal salt which is soluble in the gastro-intestinal fluids is provided as a buffer or to enhance dispersability of the guar gum or other gel-forming dietary fiber. Morever, the inclusion of a magnesium salt which is soluble in the gastro-intestinal fluids also appears to reduce still further the flushing, itching, and other usual side effects of the niacin therapy, and is accordingly preferred. The exact form in which the active ingredients are orally administered is not important, so long as the objectives of the invention are obtained. The active ingredients may take the form of the usual tablets, capsules, suspensions, dispersions, elixirs, syrups, or the like, whether administered singly or in combination, and may moreover be provided in the usual form for dietary supplements involving inclusion of a fibrous material, such as in capsules, drink mixes, breakfast foods, or the like, especially when metallic salts assisting with the internal dispersion of the guar gum or other gel-forming dietary fiber are included and/or when acids, and especially organic acids such as citric, ascorbic, malic, and tartaric are included not only to delay gelation of the guar gum or other gel-forming dietary fiber when the active ingredients are presented in the form of a drink mix but also to add a pleasant palatable flavor thereto.

DETAILED DESCRIPTION OF THE INVENTION

The following Examples are given to illustrate the invention, but are not to be construed as limiting.

EXAMPLE 1

A composition is prepared according to the following formula:

Guar gum (Cyamopsis Tetragonoloba) 400–500 mg
Niacin (nicotinic acid) 80–100 mg

These ingredients, guar gum and niacin, are blended together and encapsulated in a hard gelatine capsule. A lubricating agent may as usual be used to facilitate encapsulation. This formula can be conveniently orally ingested at an effective therapeutic dose of five (5) capsules, preferably three (3) times a day.

At a dosage of five (5) capsules, the amount of active ingredients is 2,000–2,500 mg of guar gum and 400–500 mg of niacin, close to the preferred ratio of five parts of fiber to one part of niacin.

When this dosage is taken three (3) times daily, the total amount of guar gum is 6 to 7.5 grams and the amount of niacin is 1.2–1.5 grams, an effective dosage regimen although involving less than the usually recommended daily dose of niacin when used alone.

EXAMPLE 2

In addition to the guar gum and the niacin in the amounts set forth in Example 1, magnesium carbonate is included in the composition in an amount of 80–100 mg per capsule. At a therapeutic dose of five (5) capsules, this makes the amount of magnesium carbonate 400–500 mg and, at a TID regimen, the number of capsules 15 per day, the amount of magnesium carbonate ingested then being 1.2–1.5 grams.

EXAMPLE 3

In additional formulations, calcium carbonate, aluminum hydroxide, or other physiologically-acceptable mineral salt is employed as buffer or antacid.

EXAMPLE 4

A further specific Example of a formulation according to the present invention is the following:

| Guar gum | 470 mg |
|---|---|
| Niacin | 74 mg |
| Magnesium carbonate | 74 mg |

EXAMPLE 5

Tablets are made according to the following formula:

| Each Tablet Contains | |
|---|---|
| Psyllium seed husks - powdered | 500 mg |
| Niacin | 100 mg |
| Calcium carbonate | 150 mg |
| Dextrose | 50 g |
| Citric acid | 25 mg |
| Microcrystalline cellulose (Avicel-TM) | 25 mg |

The citric acid and calcium carbonate act to mechanically disperse the gel-forming psyllium fiber which acts as a drug delivery system for the niacin. The psyllium fiber also serves to coat the niacin, minimizing its acidic effect on the stomach lining and intestines. In the foregoing formulation, some or all of the psyllium seed husk powder may be replaced by another gel-forming dietary fiber, e.g., one or more of the gums used in Example 6, pectin or a pectic substance, algal polysaccharides, glucomannan, agar, lignin, or the like, or combinations thereof, with essentially the same result.

EXAMPLE 6

Tablets are made according to the following formula:

| Each Tablet Contains | |
|---|---|
| Locust bean gum | 100 mg |
| Acacia gum | 100 mg |
| Gum arabic | 100 mg |
| Xanthan gum | 100 mg |
| Karaya gum | 50 mg |
| Tragacanth gum | 50 mg |
| Niacin | 100 mg |
| Calcium carbonate | 150 mg |
| Dextrose | 50 mg |
| Citric Acid | 25 mg |
| Microcrystalline cellulose (Avicel-TM) | 25 mg |

In the foregoing formulation, one or more of the gums may be replaced by another gel-forming dietary fiber, e.g., psyllium seed husks, pectin or a pectic substance, algal polysaccharides, glucomannan, agar, lignin, or the like, or combinations thereof, with essentially the same result.

These tablets, as well as those of Example 6, are found to be effective in lowering cholesterol levels at effective doses of niacin without the usual side effects of flushing, itching, and irritation.

EXAMPLE 7

A niacin granulate is produced in a fluid bed granulator (Glatt Air Techniques, Ramsey, N.J.). The niacin is first sprayed with NaCMC (Sodium Carboxymethylcellulose) at 7.5% solids in solution level, and 3% by weight volume percentage. While still in the fluid bed granulator, the coated niacin is then sprayed with Surelease (TM) (Colorcon, West Point, Pa.), an ethyl cellulose preparation, at 15% solids in solution and 2% by weight volume percentage.

Prepare 95% Niacin Granulation

In granulator bowl - Niacin powder.

In solution - Spray first with NaCMC, 7.5% solids in solution, 3% by weight volume percentage. Spray second with Surelease (TM) (ethyl cellulose) 15% solids, 2% by weight volume percentage.

The 95% niacin granulate is then used in the following formula:

| Each Tablet Contains | |
|---|---|
| Psyllium husk powder | 600 mg |
| Niacin granulate (95%) | 160 mg |
| Calcium carbonate | 100 mg |
| Citric Acid | 25 mg |
| Microcrystalline cellulose (Avicel-TM) | 25 mg |

In the foregoing formulation, some or all of the psyllium seed husk powder may be replaced by another gel-forming dietary fiber, e.g., one or more of the gums used in Example 6, pectin or a pectic substance, algal polysaccharides, glucomannan, agar, lignin, or the like, or combinations thereof, with essentially the same result.

A much higher dose of niacin is found to be possible by granulating the niacin before tableting so that it is released more slowly. A subject can take two tablets of the above formula with virtually no side effects such as the severe flushing, itching, or gastric distress produced by normal niacin.

EXAMPLE 8 CAPSULES

When guar or other gum, mucillage, pectin, or lignin and niacin are blended and encapsulated in capsules, the upper limit is controlled by how much powder can be put in a capsule per dosage unit. The upper limit is about 700 mg. The maximum amount of niacin one can have per capsule, and still virtually eliminate the side effects, is about 100 mg and the amount of gum or other gel-forming dietary fiber about 600 mg. However, an individual can take five (5) of these capsules at a time, for a total of 500 mg of niacin and 3,000 mg of gum or other gel-forming dietary fiber and still experience greatly reduced or virtually no side effects. If one takes five (5) capsules three times per day, this provides a very effective lipid-lowering medication, without the normal side effects associated with the same dose of niacin without the gum or other gel-forming dietary fiber, etc.

In the foregoing capsule formulation, one or more of the named gel-forming dietary fibers may be replaced by another gel-forming dietary fiber, e.g., one or more of the gums used in Example 6, algal polysaccharides, glucomannan, agar, or the like, or combinations thereof, with essentially the same result.

EXAMPLE 9 TABLETS

If niacin and a gum, e.g., guar gum or the like, are tableted, however, a different phenomena is discovered. Because of the high pressure used in the manufacture of tablets as opposed to capsules, the gum is very tightly compacted. As a result, the tablets do not dissolve as quickly. Gum tablets thus provide a very interesting drug-delivery system. An effective amount of a drug, in this case niacin, can be blended and tableted with a gum and, as it dissolves in the stomach, the tablet will slowly release the niacin out of the gum "plug". The word "plug" is used here because this is how it appears in a gastric simulator.

After twelve (12) hours in a gastric simulator with 0.1N HCl, the gum has hydrated, causing it to expand, and the tablets take on the appearance of "cotton plugs", or white balls of gum gel from which the niacin has slowly leaked. The plugs serve as a unique expendable matrix for the niacin, modulating its release into solution. The same is found to be true when these tablets are given to human subjects, as evidenced by the lack of flushing or itching side effects when two tablets, equivalent to a one-time dose of 300 mg of niacin, were given to a test panel of ten people. These same people experienced dramatic and uncomfortable flushing, itching, and irritation when they took a single dose of 250 mg of niacin without gum or other gel-forming dietary fiber.

This indicates that a higher dose of niacin per unit dosage form can be administered with gum or other gel-forming dietary fiber if the dosage form is a tablet rather than a capsule. The above formula reduces the number of dosage units required by enabling a high dose of niacin to be used. For example, an effective dose for lowering serum cholesterol can now be two tablets providing 300 mg of niacin and 1,000 mg of gum or other gel-forming dietary fiber per dose, three times per day, or 1,200 mg of niacin and 3,000 mg of gum or other gel-forming dietary fiber per day. The upper limit per dosage unit (per tablet) is about 500 mg of niacin and about 1,000 mg of gum or other gel-forming dietary fiber.

In the foregoing tablet formulation, the guar gum may be replaced in whole or in part by another gel-forming dietary fiber, e.g., one or more of the gums used in Example 6, pectin or a pectic substance, algal polysaccharides, glucomannan, agar, psyllium seed husk powder, lignin, or the like, or combinations thereof, with essentially the same result, although gums are clearly preferred.

PHARMACOLOGICAL AND CLINICAL EVALUATION

A. The cholesterol-lowering properties of the combination composition of Example 1 are examined clinically at a dosage of five (5) capsules TID, making 15 per day in all, taken at mealtime, over a period of two (2) weeks.

This is equivalent to approximately 7.05 grams of guar gum and 1.11 grams of niacin per day.

The results of the clinical study are as follows:

| Participant | Total Cholesterol Before mg/dl | Total Cholesterol After mg/dl | Difference mg/dl | % Reduction |
|---|---|---|---|---|
| M.T. | 264 | 210 | −54 | 20.5 |
| M.A. | 318 | 256 | −62 | 19.5 |
| K.E. | 262 | 220 | −42 | 12.2 |
| W.J. | 387 | 293 | −94 | 24.3 |
| O.M.M. | 236 | 212 | −24 | 10.2 |

The formulation of the invention greatly reduces the side effects of niacin, such as cutaneous flushing, resulting in itching or prickling of the skin and bright-red blushing, which is a result of the dilation of the skin capillaries and which occurs in most individuals at the beginning of treatment and whenever the dosage is increased.

B. In similar clinical tests using the formulation set forth in Example 2, the results are essentially identical. However, the amount of flushing, itching, prickling, and blushing, as subjectively experienced by the subjects in the test panel themselves and as observed by other members of the test panel, is unpredictably still further reduced. In addition, the amount of gastro-intestinal distress is substantially reduced due to the buffering effect of the magnesium carbonate employed.

C. According to the present invention, a further cholesterol-lowering study is carried out employing the combination compositions of the present invention according to Example 4. In the present study, each participant orally ingests a niacin combination composition according to the present invention having the following formula:

Dose: Five (5) capsules, TID (3 times a day)
Each capsule containing:
  74 mg niacin
  470 mg guar gum
  74 mg magnesium carbonate At a dose of five capsules, the amount of niacin is 370 mg, the amount of guar gum 2.35 g, and the amount of magnesium carbonate is 370 mg. At a dosage regimen of three times per day (TID) the amount of niacin is 1.11 grams, the amount of guar gum is 6.9 grams, and the amount of magnesium carbonate is 1.11 grams.

This dosage produces results equivalent to those set forth under "A", including a reduction in total cholesterol which averages 20.37% in the test panel of five (5) subjects, which is nearly equivalent to the results obtained using a nicotinic acid dosage of three (3) grams per day. In other words, in the present combination, a daily dosage of niacin which amounts to one-third of the daily dose, usually employed for niacin alone, is capable of lowering total cholesterol to approximately the same degree, and without the intolerable side effects ordinarily produced by niacin alone at such dosage levels.

Alternatively, the clinical study can be observed by administering the active ingredients nicotinic acid and guar gum or other gel-forming dietary fiber simultaneously. As already pointed out, calcium carbonate or other mineral carbonate can be substituted for the magnesium carbonate, although a magnesium salt such as magnesium carbonate, magnesium oxide, or magnesium hydroxide, but preferably magnesium carbonate, produces unobvious and clear-cut advantages, as already set forth.

In an extension of the clinical evaluation set forth in the foregoing under "C", subject No. 1 after seventeen

(17) days and subject No. 2 after eighteen (18) days were evaluated from the standpoint of effect upon different types of blood components, the following cumulative summary report indicating for No. 1 as follows:

|  | Day 1 | Day 23 |
| --- | --- | --- |
| Cholesterol | 387 | 293 MG/DL |
| Triglyceride | 357 | 198 MG/DL |
| HDL-C | 39 | 42 MG/DL |
| LDL-C | 277 | 211 MG/DL |
| VLDL-C | 71 | 40 MG/DL |
| LDL-C/HDL-C | 7.0 | 5.0 |
| Chol/HDL-C | 9.9 | 7.0 |

With respect to subject No. 2, the following cumulative summary report shows the results after eighteen days according to the suggested five (5) capsule dosage TID using the combination composition of Example 4 hereof.

|  | Day 1 | Day 18 |
| --- | --- | --- |
| Cholesterol | 264 | 210 MG/DL |
| Triglyceride | 101 | 70 MG/DL |
| HDL-C | 53 | 56 MG/DL |
| LDL-C | 191 | 140 MG/DL |
| VLDL-C | 20 | 14 G/DL |
| LDL C/HDL-C | 3.6 | 2.5 |
| Chol/HDL-C | 5.0 | 3.7 |

From the foregoing, it is clear that in both cases the HDL cholesterol percentage was increased while the LDL cholesterol and the VLDL cholesterol was substantially reduced, as well as total cholesterol and triglyceride content, and that the ratios of LDL-C to HDL-C and Chol/HDL-C dropped considerably.

Extremely noteworthy is the improved LDL/HDL ratio, which is indicative of a reduced risk for heart disease according to established interpretation of such results.

D. Further Clinical Evaluation

In addition to the foregoing data, in further tests conducted and reported to me, two (2) subjects were continued in the foregoing study for thirty (30) days in order to provide a more accurate evaluation of the effectiveness of the formulation (known as LONI-CIN)(TM) and to examine the results of full lipid panels. For those two patients here involved, measurements of cholesterol levels, triglyceride levels, high density lipoproteins, low density lipoproteins, and very low density lipoproteins were taken. The results in these patients after thirty days were as follows:

|  | Day 1 | Day 30 |
| --- | --- | --- |
| Cholesterol | 292 | 175 |
| LDL Cholesterol | 212 | 103 |
| HDL Cholesterol | 33 | 33 |
| LDL/HDL | 6.42 | 3.12 |
| Cholesterol | 271 | 194 |
| LDL Cholesterol | 163 | 105 |
| HDL Cholesterol | 45 | 57 |
| LDL/HDL | 3.62 | 1.84 |

It is to be noted that the reduction in LDL, the most dangerous form of cholesterol, was 49 to 50% in the first patient, and 35% in the second patient.

From the foregoing, it is clear that, in both cases, the HDL cholesterol percentage was increased (an advantageous effect) whereas the LDL cholesterol and the VLDL cholesterol percentage was substantially reduced, as well as total cholesterol and triglyceride content, and that the ratios of LDL cholesterol to HDL cholesterol and cholesterol/HDL cholesterol dropped considerably, a very desirable result. Extremely noteworthy is the improved LDL/HDL ratio, which is indicative of a reduced risk for heart disease according to established interpretation of such results.

Since these patients were treated in the same PHARMACOLOGICAL AND CLINICAL EVALUATION A. as reported in the foregoing, but for a period of thirty (30) days rather than the two (2) weeks reported in the foregoing tabulation, the effectiveness of the guar/niacin product of the invention in lowering serum cholesterol and in effecting the foregoing advantageous results is accordingly not subject to dispute, and the undesirable flushing is clearly minimized or eliminated by using the guar/niacin of the invention.

E. Further Clinical Evaluation

Twelve (12) subjects were selected randomly by a cardiologist from those of his cardiology patients considered to be prime candidates for reduction in serum cholesterol, the patients selected being between the ages of thirty-two (32) and sixty-seven (67). Excluded from the test were patients having a history of peptic ulcer, irritable colon, and inflammatory bowel disease. Also excluded from the test were patients having a plasma triglyceride level greater than 350.

The study was conducted over a period of three (3) days. It was designed to compare the side effects of a single dose of approximately 240 mg of niacin administered orally alone, as a single tablet containing about 250 mg of niacin, or as three (3) capsules containing the formula set forth below and totaling 240 mg of niacin.

On the first day, each subject took the one 250 mg niacin tablet orally immediately after breakfast. Eight (8) of the twelve (12) patients in the study experienced flushing shortly after taking the niacin tablet.

On the second and third days, each of the patients took three (3) capsules of the guar/niacin preparation orally immediately after breakfast. Each capsule contained the following:

| guar gum | 520 mg |
| --- | --- |
| niacin | 80 mg |
| magnesium carbonate | 80 mg, | the foregoing ingredients being in particulate form, that is, granulated or powdered, and encapsulated in a hard gelatin capsule for oral administration.

Following is a summary of the results obtained in this study.

|  | Number of Subjects | Single dose of Niacin | Number of subjects experiencing severe Side Effects in particular Flushing |
| --- | --- | --- | --- |
| Niacin | 12 | 250 mg | 8 |
| Niacin/Guar | 12 | 240 mg | 0 |

The results of the above-identified clinical study were reported by the individuals selected for the study and in some cases were confirmed by personal observation. Almost all of the patients selected for the study found the single dose of niacin objectionable from the standpoint of side effects. Eight (8) patients experienced severe side effects and in particular the usual flushing.

The same individuals reported that no flushing was experienced upon ingestion of the capsules containing the niacin and guar gum. The same individuals participating in the test had no adverse comments concerning the combination of niacin with guar gum and, in addition to finding that the undesirable flushing effect of the niacin was not experienced upon ingestion of the niacin/guar gum capsules, found this formulation to be otherwise unobjectionable and acceptable.

From the results of this study, it is clear that the niacin/guar gum formulation essentially eliminated the unpleasant flushing and other side effects (e.g., prickling and itching) which are usually associated with niacin alone or in usual formulations thereof.

The adverse side effects experienced by eight of the twelve patients participating in the study, or approximately 75%, is not out of line with usual experience employing niacin alone. In fact, even time-release niacin formulations at a dosage as low as 250mg were recently reported to produce undesirable flushing and related side effects in 24% of the patients treated therewith in a published study by Luria, M. H., Arch. Intern. Med. 148, 2493-2495 (November 1988).

In the present study, the combination of niacin with guar gum substantially reduced or essentially eliminated the undesirable side effects of niacin, in particular severe flushing, upon oral administration thereof, such flushing being usually associated with niacin when taken alone or in usual formulations.

In any of the foregoing formulations, one gel-forming dietary fiber may be replaced in whole or in part by another gel-forming dietary fiber, e.g., one or more of the gums used in Example 6, pectin or a pectic substance, algal polysaccharides, glucomannan, agar, lignin, or the like, or combinations thereof, with essentially the same result.

According to Arch. Intern. Med. 148, 2493-2495 (Nov. 1988), "Effect of Low-Dose Niacin on High-Density Lipoprotein Cholesterol, and Total Cholesterol/Density Lipoprotein Cholesterol Ratio", Luria M. H., subjects were given four 250 mg capsules of time-release niacin per day for a total of one gram per day. The subjects were started on one 250 mg capsule per day for the first week. Fifty-five patients were initially started on niacin. Even at 250 mg per day of time-release niacin, 24% of the patients (13) dropped out due to side effects. An additional eight patients of the remaining 42 dropped out after achieving the one gram per day dose of niacin, due to side effects. Practically every patient experienced flushing for the first few weeks.

In short, Luria summarizes today's crucial issue in his comments on page 2495 of the above-cited paper by stating "There is little question that the side effects of niacin in usual pharmacologic doses limit the usefulness of the drug. In one study (Schoch HK: The U.S. Veterans Administration Cardiolgy Drug Lipid Study: An interim report in Adv. Exp. Med. Biol 4, 405-420 (1969), only 28% of the patients could maintain a target dose of 4 g/d (grams per day); 40 were maintained at approximately 2 g/d, and 32% discontinued the drug altogether." Overall, 40% of the subjects dropped out of the study at some point due to side effects.

The foregoing provide a good indication of the widespread problems presently associated with the use of niacin for reduction of serum cholesterol, which are solved or at least greatly alleviated according to the present invention.

According to the practice of the art, the niacin or nicotinic acid may be provided as such or in the form of a prodrug thereof, numerous of which are presently available and which break down, to a greater or lesser extent upon ingestion, to provide nicotinic acid in the system of the subject orally ingesting the same for reduction or control of cholesterol levels in the said subject. Representative prodrugs of this type are derivatives of nicotinic acid, especially esters, and the like, and many of these prodrugs are also subject to the same side effects as niacin itself, namely, the production of the undesirable and sometimes intolerable side effects of flushing, itching, and the like and, to the extent that these prodrugs do provide an effective antihyperlipidemic amount of nicotinic acid upon ingestion, as well as the undesirable side effects of niacin previously mentioned, they may be employed according to the present invention in lieu of niacin itself, the method and combination compositions of the present invention providing effective cholesterol-lowering effect as well as reduction or essential elimination of the undesirable effects of niacin when such a prodrug is employed just as in the case of the employment of niacin itself.

As already stated, in a particularly preferred embodiment according to the present invention, a physiologically-acceptable soluble magnesium salt is administered simultaneously together with the active ingredients according to the present invention, namely, niacin and guar gum or other gel-forming dietary fiber, and most preferably in a combination composition together therewith. The inclusion of the physiologically-acceptable magnesium salt appears to still further reduce the flushing and related side effects of the niacin and such magnesium salt may illustratively but not limitatively be or comprise magnesium carbonate, magnesium chloride, magnesium oxide, magnesium hydroxide, or any other physiologically-acceptable salt of magnesium with either a mineral or organic acid which is soluble, that is, capable of dissolution in the gastric fluids.

According to one preferred embodiment of the present invention, the active ingredients, namely, niacin and guar gum or other gel-forming dietary fiber, are provided in granular form for addition to water to provide a drinkable form of oral administration. When employed in this form, a quantity of a food-grade acid, also in powder or granular form, which is effective in extending the time for gelation of the resulting mix upon addition of or to water, is also preferably supplied concurrently or simultaneously with the aforementioned active ingredients and, in the most preferred form, is provided in the form of a granular mix together with the other active ingredients so as to provide a combination granular mix composition. When the composition and the method of the present invention are so constituted and/or administered, the food-grade acid employed is preferably an organic acid such as citric, ascorbic, tartaric, or malic, which provides a tasty and palatable flavor while at the same time providing effectiveness for extending the time for gelation of the resulting mix upon the addition of or to water.

In another preferred embodiment according to the present invention, an orally-ingestible non-toxic mineral salt capable of dissolution in the gastric fluids is also administered simultaneously with the active ingredients, namely, niacin and guar gum or other gel-forming dietary fiber, preferably in a combination composition therewith and, when the active ingredients according to the present invention are so constituted or administered, the orally-ingestible non-toxic mineral salt capable of dissolution in the gastric fluids assists with more rapid and complete internal dispersion of the guar gum or other gel-forming dietary fiber in the gastrointestinal tract, and is preferably selected from the group consisting of calcium carbonate, magnesium carbonate, and potassium carbonate.

It is therefore seen that the present invention provides an oral antihyperlipidemic composition of nicotinic acid (niacin) characterized by reduced and related flushing effects comprising as active ingredients nicotinic acid and guar gum or another gel-forming dietary fiber, which is effective in lowering of cholesterol levels, especially LDL cholesterol levels, without the usual undesirable flushing, itching, and related side effects of niacin, and a method of lowering cholesterol levels by employment of such an oral pharmaceutical or dietary supplement composition, or by the simultaneous oral administration of the active ingredients thereof, all having the unpredictable and highly advantageous characteristics and effects as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. An oral antihyperlipidemic composition of nicotinic acid, having a reduced flushing effect, comprising an effective antihyperlipidemic amount of nicotinic acid and an effective cutaneous-flushing-reducing amount of a gel-forming dietary fiber.

2. A composition of claim 1 wherein the composition contains at least about 50 mg of nicotinic acid.

3. A composition of claim 1 wherein the amount of dietary fiber is at least about 250 mg.

4. A composition of claim 2 wherein the amount of dietary fiber is at least about 400 mg, in capsule or tablet form.

5. A composition of claim 2 wherein the amount of dietary fiber is at least about 400 mg, and an antacid.

6. A composition of claim 4 comprising also an orally-ingestible non-toxic mineral salt capable of dissolution in the gastric fluids.

7. A composition of claim 6 wherein the mineral salt is a physiologially-acceptable magnesium salt.

8. A composition of claim 6, wherein the mineral salt is selected from the group consisting of calcium carbonate, magnesium carbonate, and potassium carbonate.

9. A composition of claim 1, wherein the active ingredients are in granular form and comprising also a quantity of a food-grade acid in powder or granular form which is effective in extending the time for gelation of the resulting mix upon addition of water.

10. A composition of claim 9, wherein the food-grade acid is selected from the group consisting of citric acid, ascorbic acid, tartaric acid, and malic acid.

11. A composition of claim 8 comprising
about 400–500 mg gel-forming dietary fiber
about 80–150 mg nicotinic acid
about 80–100 mg magnesium carbonate.

12. Method for reducing the cutaneous flushing caused by the administration of an effective antihyperlipidemic amount of nicotinic acid to a patient suffering from hyperlipidemia, comprising the step of simultaneously orally administering to said patient an effective cutaneous-flushing-reducing amount of a physiologically-acceptable gel-forming dietary fiber and an effective antihyperlipidemic amount of nicotinic acid.

13. Method of claim 12 wherein the nicotinic acid and dietary fiber are in the form of a pharmaceutical composition containing both active ingredients.

14. Method of claim 13 wherein the active ingredients are in capsule or tablet form.

15. Method of claim 14 comprising also administration of a physiologically-acceptable mineral salt.

16. Method of claim 13, wherein a single dose comprises about 300–1000 mg of niacin and about 1.5–6 g of dietary fiber.

17. Method of claim 15, wherein a single dose comprises about 300–1000 mg niacin, about 1.5–6 g of dietary fiber, and about 300–500 mg of a physiologically-acceptable mineral salt.

18. Method of claim 12 wherein a dosage unit comprises at least about 250 mg dietary fiber and at least about 50 mg niacin.

19. Method of claim 16 wherein a single dose comprises at least about 2 g dietary fiber and at least about 350 mg of niacin.

20. Method of claim 15 wherein a daily dose comprises at least about 6 g dietary fiber, at least about 1 g niacin, and at least about 1 g magnesium carbonate.

21. Method of claim 12, wherein an orally-ingestible non-toxic mineral salt capable of dissolution in the gastric fluid is simultaneously orally administered.

22. Method of claim 21 wherein the non-toxic mineral salt is a physiologically-acceptable magnesium salt.

23. Method of claim 22 wherein the physiologically-acceptable magnesium salt is magnesium carbonate.

24. Method of claim 12, wherein the active ingredients are in granular form and wherein a quantity of a food-grade acid also in powder or granular form which is effective in extending the time for gelation of the resulting mix upon addition of water is also concurrently or simultaneously orally administered.

25. Method of claim 24, wherein the food-grade acid is selected from the group consisting of citric acid, ascorbic acid, tartaric acid, and malic acid.

26. Method of claim 21, wherein the mineral salt is selected from the group consisting of calcium carbonate, magnesium carbonate, and potassium carbonate.

27. Method of claim 15, wherein the mineral salt is a physiologically-acceptable magnesium salt.

28. A composition of claim 6, wherein the mineral salt is a pharmacologically-acceptable mineral salt capable of dissolution in the gastric fluid with release of gas.

29. A composition of claim 28, wherein the gas is carbon dioxide.

30. Method of claim 21, wherein the mineral salt is a pharmacologically-acceptable mineral salt capable of dissolution in the gastric fluid with release of gas.

31. Method of claim 30, wherein the gas is carbon dioxide.

32. Composition of claim 29, wherein the mineral salt is a carbonate or bicarbonate.

33. Method of claim 31, wherein the mineral salt is a carbonate or bicarbonate.

34. A composition of claim 9, comprising also a pharmacologically-acceptable mineral salt capable of dissolution in the gastric fluid with release of gas.

35. A composition of claim 34, wherein the mineral salt is a carbonate or bicarbonate.

36. Method of claim 12, wherein a daily dose comprises at least about 6 g dietary fiber and at least about 1 g niacin.

37. A composition of claim 1, wherein the ratio of guar gum by weight to nicotinic acid by weight is at least 3:1.

38. Method of claim 12, wherein the ratio of guar gum by weight to nicotinic acid by weight is at least 3:1.

39. A composition of claim 37, wherein the ratio of guar gum by weight to nicotinic acid by weight is about 3:1 to about 8.3:1.

40. Method of claim 38, wherein the ratio of guar gum by weight to nicotinic acid by weight is about 3:1 to about 8.3:1.

* * * * *

UNITED STATES PATENT AND TRADEMARK OFFICE
CERTIFICATE OF CORRECTION

PATENT NO. : 5,023,245

DATED : Jun. 11, 1991

INVENTOR(S) : Eric H. Kuhrts

It is certified that error appears in the above-identified patent and that said Letters Patent is hereby corrected as shown below:

Title Page,[63],Related U.S. Application Data, third line;
   "1988, and" should read -- 1988, now abandoned; and --.

Column 1, line 7; "1988;" should read -- 1988, now abandoned; --.

Column 1,. line 37; "lis of" should read -- lism of --.
Column 7, line 2; "i the" should read -- in the --.
Column 7, line 10; "the of" should read -- the time for gelation
   of --.
Column 13, line 6/7; Table, heading of 3rd column; "23"
   should read -- 17 --.
Column 13, 2nd table, line 26;"14 G/DL" should read -- 14 MG/DL --.
Column 17, line 53; "physiologially-acceptable" should read
   -- physiologically-acceptable --. (Amdt. 1-31-91, P. 1)

Signed and Sealed this

Third Day of November, 1992

Attest:

DOUGLAS B. COMER

Attesting Officer

Acting Commissioner of Patents and Trademarks